United States Patent [19]

Déziel

[11] Patent Number: 4,788,282
[45] Date of Patent: Nov. 29, 1988

[54] DEPROTECTION OF ALLYLIC ESTERS AND ETHERS

[75] Inventor: Robert Déziel, Quebec, Canada

[73] Assignee: Bristol-Myers Company, New York, N.Y.

[21] Appl. No.: 742,495

[22] Filed: Jun. 7, 1985

[51] Int. Cl.[4] .......................................... C07D 513/04
[52] U.S. Cl. ................................................. 540/350
[58] Field of Search ........................................ 540/350

[56] References Cited

U.S. PATENT DOCUMENTS

| 4,314,942 | 2/1982 | McCombie | 260/245.2 |
| 4,536,335 | 8/1985 | Kim et al. | 260/245.2 T |
| 4,658,039 | 4/1987 | Samaan | 548/501 |

OTHER PUBLICATIONS

Mitsuaki Ohtani et al., J. Org. Chem. 1984, 49, 5271–5272.
Paul D. Jeffrey et al., J. Org. Chem. 1982, 47, 587–590.
H. Kunz et al., Angew. Chem. Int. Ed. Engl. 23 (1984) pp. 71–72.

*Primary Examiner*—Robert Gersil
*Attorney, Agent, or Firm*—Robert E. Carnahan

[57] ABSTRACT

A process is disclosed for the deprotection of allylic esters and ethers. The process comprises reacting an allyl ester of a carboxylic acid or an allyl ether of a phenol with pyrrolidine or piperidine and a catalytic amount of an organic-soluble palladium complex having a coordinating phosphine ligand to cleave the allyl moiety. The resultant carboxylic acid or phenol is then recovered.

5 Claims, No Drawings

DEPROTECTION OF ALLYLIC ESTERS AND ETHERS

BACKGROUND OF THE INVENTION

This invention relates to the palladium-catalyzed deprotection of allylic esters and ethers.

It is well known to use the allyloxycarbonyl group as a protecting group for a carboxylic acid, i.e., to esterify the carboxylic acid with allyl alcohol and to thereafter remove the allyloxycarbonyl group to convert the carboxylic acid group back to its original form after it has served its protecting function. For example, Ohtani et al in *Journal of Organic Chemistry*, 1984, Vol. 49, pps. 5271–5272, report that one crucial step in the synthesis of carbapenems is the final deprotection step of the C-3 ester function and cite as one example the cleavage of the allyl ester group by the action of palladium(0).

The following references all disclose cleavage of the allyloxycarbonyl function in carboxyl protected beta-lactam derivatives, such as penicillins, cephalosporins, and carbapenems, using potassium 2-ethylhexanoate in the presence of a catalytic amount of tetrakis(triphenylphosphine)-palladium(0) and triphenylphosphine:

Jeffrey et al, *Journal of Organic Chemistry*, 1982, Vol. 47, pps. 587–590;
U.S. Pat. No. 4,314,942;
U.K. Pat. appln. No. GB 2 128 187A, published Apr. 26, 1984, Example 21.

Kunz et al, *Angew. Chem. Int. Ed. Engl.*, 1984, Vol. 23, pps. 71-72 report on the use of the allyl group as a removable carboxy-protecting group for the synthesis of labile O-glycopeptides. This article reports on the cleavage of the allyl ester moiety by reaction with about ten mole percent of tetrakis(triphenylphosphine)palladium(0) under argon in tetrahydrofuran and in the presence of a ten fold excess of morpholine as an acceptor nucleophile.

It is an object of this invention to provide a process for the deallylation of allyl esters and phenolic ethers which results in higher yields of the corresponding carboxylic acid or phenol then prior art processes.

It is a further object of this invention to provide such a process which can be conducted at lower temperatures and in shorter reaction times than prior art processes, thereby making possible its application to allyl esters having sensitive structural features that might be decomposed under reaction conditions involving higher temperatures and longer reaction times.

SUMMARY OF THE INVENTION

The objects of this invention are attained by a process which comprises reacting an allyl ester of a carboxylic acid or an allyl ether of a phenol with pyrrolidine or piperidine and a catalytic amount of an organic-soluble palladium complex having a coordinating phosphine ligand to cleave the allyl moiety. The resultant carboxylic acid or phenol is then recovered.

DETAILED DESCRIPTION OF THE INVENTION

The process of this invention may be utilized for the deallylation of any allyl ester of a carboxylic acid or allyl ether or a phenol, e.g., allylphenyl ether, the allyl ester of benzoic acid, the allyl ester of cinnamic acid, etc. A preferred class of allyl esters which may be deprotected in accordance with the practice of this invention, are beta-lactam allyl esters such as penicillins, cephalosporins, and carbapenems. Particularly preferred are allyl esters of carbapenem derivatives, said derivatives being characterized by a 2-substituent of the formula

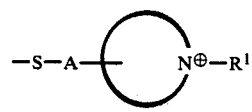

in which A represents a $C_1$–$C_6$ straight or branched chain alkylene group; $R^1$ represents an optionally substituted aliphatic, cycloaliphatic, cycloaliphatic-aliphatic, aryl, araliphatic, heteroaryl, heteroaraliphatic, heterocyclyl or heterocyclyl-aliphatic radical and

represents a nitrogen-containing aromatic heterocycle attached to the alkylene group A at a ring carbon atom and quanternized by substituent $R^1$. Such derivatives are described in detail in U.K. patent application No. GB No. 2 128 187A, the disclosure of which is incorporated herein by reference.

The preferred organic-soluble palladium complex catalyst useful in the process of this invention is tetrakis(triphenylphosphine)palladium(0) and it is preferably utilized in the presence of free triphenylphosphine. It is preferred to use from 0.01 to 0.1 mole of catalyst per mole of allyl ester or ether. It is also preferred to use from 1.5 to 5 moles of triphenylphosphine per mole of tetrackis(triphenylphosphine)palladium.

The amount of pyrrolidine or piperidine used in the reaction is preferably from 1.0 to 1.5 moles per mole of allyl ester or ether.

The deallylation reaction is preferably conducted in an inert solvent such as dichloromethane, chloroform, ethyl ether, benzene, toluene, ethyl acetate, acetonitrile, etc. It is preferred to conduct the reaction at a temperature of from $-5°$ C. to $30°$ C. for a time of from 10 minutes to 4 hours.

The following examples illustrate the best modes contemplated for carrying out this invention.

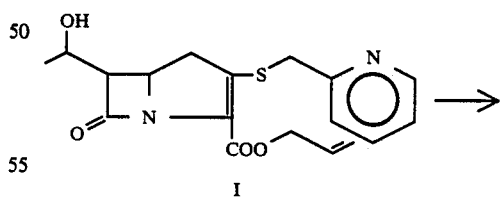

I

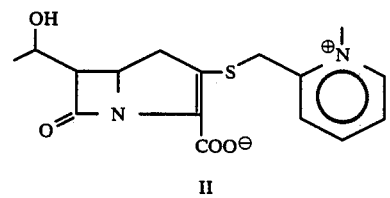

II

Methyl trifluoromethanesulfonate (1.05 equivalent) was added to an ice cooled suspension of compound I, obtained as described in Step F, Example 21 of U.K.

patent application No. GB 2128187A, in acetonitrile. After 20 minutes, triphenylphosphine (5% mole), tetrakis(triphenylphosphine)palladium(0) (2.5% mole) and pyrrolidine (1.05 equivalent) were added. Precipitation occurred rapidly and the resulting slurry was stirred for 10 minutes at 0° C. After adding acetone, the crude solid was isolated and crystallized from methanol to give the desired product, II, in 70% yield and with 90–93% purity.

When potassium 2-ethylhexanoate is substituted for pyrrolidine in Example 1, no product is obtained.

EXAMPLE 2

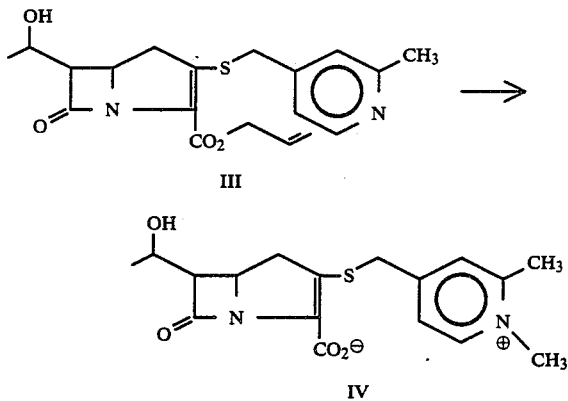

III

IV

A solution of the allyl ester, compound III, (0.350 g, 0.936 mmol) in 6 mL of dry acetonitrile was cooled at −5° C. and treated with methyl trifluoromethanesulfonate (0.111 mL, 0.983 mmol). After 15 minutes, a solution of tetrakis(triphenylphosphine)palladium (0.027 g, 25 mol %) and triphenylphosphine (0.027 g) was added. After stirring the reaction mixture for 5 minutes, pyrrolidine (0.082 mL, 0.983 mmol) was added dropwise. A solid slowly began to separate from the resulting brown solution. The mixture was vigorously stirred at 0° C. for 20 minutes, then 15 mL of cold (0° C.) acetone was slowly added and stirring was continued at 0° C. for 20 minutes. The resulting suspension was filtered and the residue was washed with cold acetone and then dried to vacuo to give 0.345 g of a beige powder. This material was taken up in a small amount of pH 7 phosphate buffer (0.05M) and applied to a short reverse-phase (C18 BondaPak) column. Elution with H2O and lyophilization of the relevant fractions gave 0.255 g of a light yellow solid. This material was rechromatographed, as done before, to afford (after lyophilization) pure compound IV (0.195 g, 60% yield) as a light yellow solid: $^1$Hnmr (D$_2$O) $\delta$8.58, 7.83 (ABq, J=6.4 Hz, 2H), 7.87 (s, 1H), 4.32–3.95 (m, 2H), 4.22 (s, 2H), 4.17 (s, 3H), 3.32 (dd, J$_1$=2.6 Hz, J$_2$=6.1 Hz, 1H), 3.06–2.93 (m, 2H), 2.74 (s, 3H), 1.22 (d, J=6.4 Hz, 3H); ir (KBr) 1757, 1590 cm$^{-1}$; uv (phosphate buffer, pH 7.4) 296 nm ($\epsilon$7446).

EXAMPLE 3

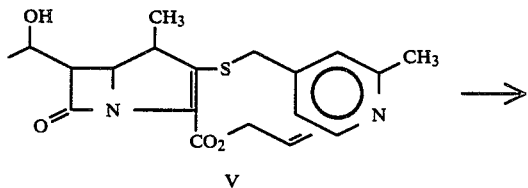

V

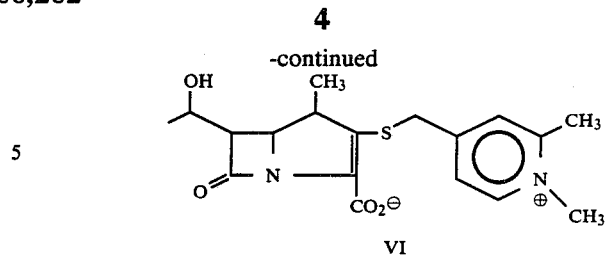

VI

A solution of the allyl ester, compound V, (0.582 g, 0.0015 mol) in 15 mL of dry acetonitrile was treated with methyl trifluoromethanesulfonate (0.178 mL, 1.575 mmol) at −5° C. under N$_2$. After 15 minutes, a solution of tetrakis(triphenylphosphine)palladium (0.035 g, 2 mol %) and triphenylphosphine (0.035 g) in 1 mL of methylene chloride was added, followed after 5 minutes by 0.131 mL (1.575 mmol) of pyrrolidine. The resulting mixture was stirred at 0° C. for 20 minutes and then 30 mL of cold (0° C.) acetone was added. The mixture was vigorously stirred at 0° C. for 15 minutes and then the precipitate was collected by filtration, washed with cold acetone and dried in vacuo to give 0.520 g of a beige powder. By diluting the filtrate with ether, another 0.041 of the crude product was obtained. The combined solids were dissolved in a small about of pH 7.4 phosphate buffer (0.05M) and applied to a reverse-phase (C18 BondaPak) column. Elution with H$_2$O and then 2% acetonitrile-H$_2$O afforded, after lyophilization, compound IV (0.413 g, 76% yield) as a yellow solid: $^1$Hnmr (D$_2$O) $\delta$8.55, 7.76 (ABq, J=6.3 Hz, 2H), 7.81 (s, 1H), 4.4–3.7 (m, 2H), 4.19 (s, 2H), 4.16 (s, 3H), 3.47–3.14 (m. 2H), 2.73 (s, 3H), 1.24 (d, J=6.4 Hz, 3H), 1.16 (d, J=7.3 Hz, 3H), ir (KBr) 1750, 1595 cm$^{-1}$; uv (phosphate buffer, pH 7.4) 293 nm ($\epsilon$7170).

EXAMPLE 4

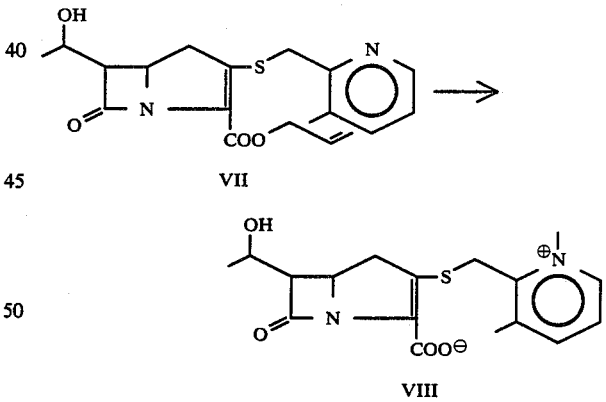

VII

VIII

To an ice-cooled suspension of the allyl ester, compound VII (10.00 g, 26.7 mmol) in 100 mL of acetonitrile was added methyl trifluoromethanesulfonate (3.17 mL, 28.05 mmol). The resulting homogeneous yellow solution was stirred at 20° C. Triphenylphosphine (350 mg, 1.33 mmol) and tetrakis(triphenylphosphine)palladium (770 mg, 0.66 mmol) in 20 mL of methylene chloride were successively added, the mixture was stirred 5 minutes and then a solution of pyrrolidine (2.4 mL, 28.05 mmol) in 15 mL of acetonitrile was added over a 5 minutes period. Crystallization occurred and the resulting slurry was stirred at 0° C. for 10 minutes. Pre-cooled acetone (150 mL) was added and the mixture was stirred 15 minutes. The resultant yellow solid was collected and washed twice with 60 mL of acetone. After drying, the yellow solid was triturated in 50 mL of cold (0° C.) methanol for 30 minutes. The resultant beige paste was filtered, partially dried, and dissolved in 20 mL of cold water. The resulting mixture was filtered quickly and 100 mL of cold ethanol were added. After stirring at 0° C. for about 10 minutes, crystallization occurred and the resulting mixture was stirred 1.3 hours more. The solid was collected and dried under high vacuum for 3 hours to obtain compound VIII, 4.82 g, 51.8% yield.

EXAMPLE 5

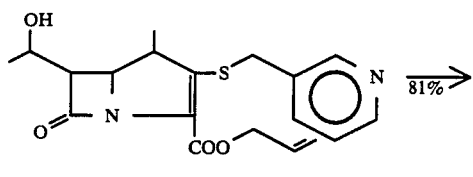

IX

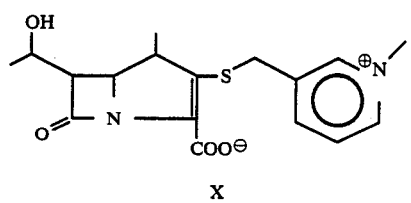

X

A solution of the allyl ester, compound IX (12.63 g, 33.707 mmol) in 124 mL of acetonitrile was treated at 0°–5° C. under a nitrogen atmosphere by adding dropwise methyl trifluoromethanesulfonate (4.055 mL, 35.349 mmol). The clear yellow reaction mixture was stirred for 15 minutes at 0°–5° C. To this reaction mixture maintained at 0°–5° C. was added at once triphenylphosphine (429.44 mg, 1.661 mmol), followed by a solution of tetrakis(triphenylphosphine)palladium (959.56 mg 0.831 mmol) in 33 mL of methylene chloride. The clear orange reaction mixture was stirred at 0°–5° C. for 5 minutes. There was then added dropwise a solution of pyrrolidine (3.03 mL, 33.707 mmol) in acetonitrile (41.3 mL). To this clear dark orange reaction mixture, which was stirred 5 minutes at 0°–5° C., was added, portion wise and with vigorous stirring, ice-cold acetone (250 mL) followed by anhydrous diethyl ether (150 mL). Stirring was continued for 5 minutes at 0°–5° C., and the suspension was then filtered quickly under a stream of nitrogen. The solid residue was washed with anhydrous diethyl ether (50 mL) and vacuum dreied to obtain 11.05 g (33.12 mmol, yield 96.6%) of compound X as a crude yellow hygroscopic solid. The solid was dissolved in ice-cold phosphate buffer (75 mL; pH 7.0) and was washed twice with 50 mL portions of diethyl ether. The aqueous layer was vacuum pumped with stirring for 45 minutes and was purified by reversed phase chromotography. After purification and lyophilization, 9.63 g (27.617 mmol, yield 81.0%) of compound X was obtained.

EXAMPLES 6 AND 7

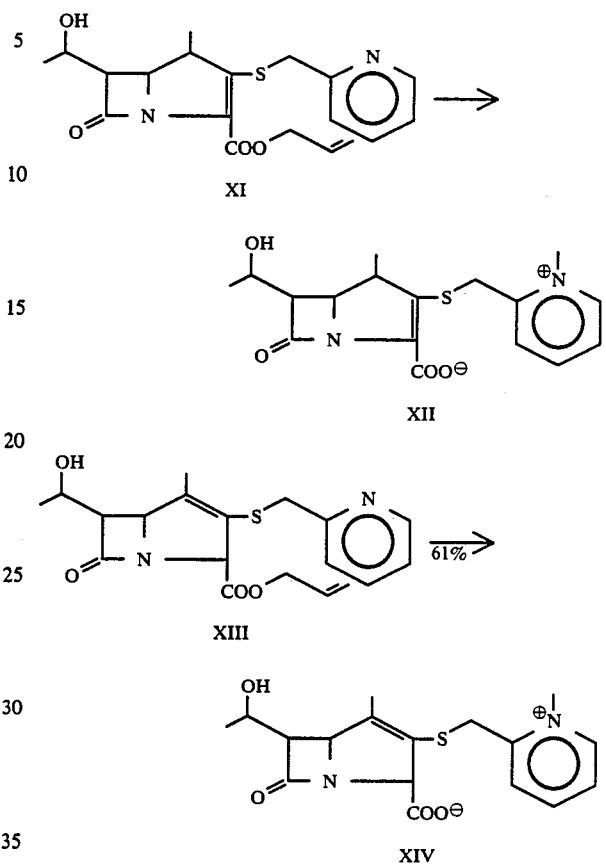

Utilizing procedures similar to those described in Examples 1–5, the above reactions were conducted. Compound XII was obtained in a 72% yield and Compound XIV was obtained in a 61% yield.

The following example illustrates the use of piperidine instead of pyrrolidine in the practice of this invention.

EXAMPLE 8

The reaction illustrated in Example 1 was conducted as follows: To a suspension of the allyl ester, compound I (350 mg, 0.971 mmol) in 10 mL of acetonitrile, cooled to 0° C., was added methyl trifluoromethanesulfonate (0.121 mL, 1.068 mmol). The resulting light yellow mixture was stirred 1 hour and triphenylphosphine (25 mg, 0.095 mmol) and tetrakis(triphenylphosphine)palladium (25 mg, 0.0216 mmol) in 2 mL of methylene chloride were added. Piperidine (0.105 mL, 1.068 mmol) was slowly added and the resulting light orange mixture was stirred at 0° C. After 15 minutes, a yellow precipitate formed and stirring was continued for 1½ hours. Acetone (10 mL) was added and the resulting slurry was stirred 30 minutes, the solid was filtered and washed with two 10 mL portions of acetone and dried. The resultant product, 230 mg, 70.7% yield, had a purity of about 69.4%.

The following example illustrates the process of this invention applied to the deallylation of a cephalosporin.

EXAMPLE 9

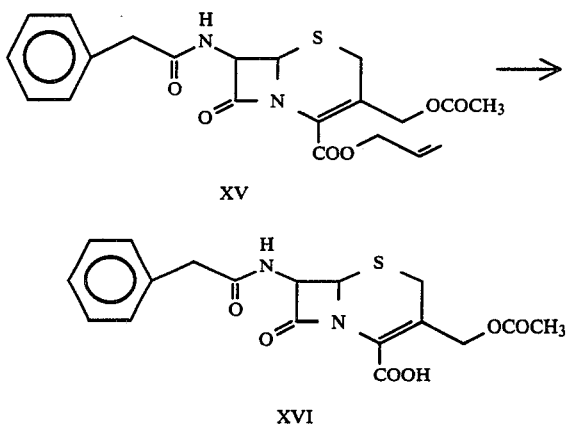

XV

XVI

To an ice-cooled solution of the allyl ester, compound XV (787 mg, 1.828 mmol), tetrakis(triphenylphosphine)palladium(0) (53 mg, 0.045 mmol) and triphenylphosphine (50 mg, 0.190 mmol) in 10 mL of methylene chloride was slowly added pyrrolidine (0.161 mL, 1.919 mmol). The mixture was stirred at 0° C. for 25 minutes and was then poured into 10 mL of a diluted solution of sodium bicarbonate (383 mg). After vigorous agitation, the organic phase was separated and extracted again with 10 mL of diluted sodium bicarbonate. The aqueous solution was then acidified to pH 2.5 at 0° C. with 1N HCl to which 10 mL of methylene chloride had been previously added. The organic phase was separated and the aqueous solution was extracted with another 10 mL of methylene chloride. After drying and evaporation in vacuo, 630 mg of the free acid, compound XVI, was obtained (88% yield).

The following two examples illustrate the deallylation process applied to allyl esters of penicillins.

EXAMPLE 10

To an ice-cooled mixture of the allyl ester of penicillin-V (540 mg, 1.38 mmol) and tetrakis(triphenylphosphine)palladium (40 mg, 0.0345 mmol) in 10 mL of methylene chloride was added pyrrolidine (0.121 mL, 1.45 mmol). The mixture was stirred at 0° C. for 30 minutes and then extracted with 10 mL of aqueous sodium bicarbonate (600 mg). The solution was then acidified with 5 HCl and extracted portions of methylene chloride. After drying and evaporation in vacuo, 301 mg (62.3% yield) of penicillin-V free acid was isolated as a white solid. The NMR spectrum was consistent with the structure of penicillin-V free acid.

EXAMPLE 11

To a solution of the allyl ester of penicillin-G (1.456 g; 3.889 mmol) in 20 mL of methylene chloride were added tetrakis(triphenylphosphine)palladium (112 mg, 0.097 mmol) and triphenylphosphine (100 mg, 0.381 mmol). After stirring a few minutes, a homogeneous mixture was obtained. The mixture was then cooled down to 0° C. and pyrrolidine (0.341 mL, 4.084 mmol) in 5 mL of methylene chloride was added slowly. The resulting mixture was stirred 15 minutes at 0° C. Diluted sodium bicarbonate (25 mL), prepared by dissolving 1.63 g of sodium bicarbonate in 50 mL of water, and 10 mL of ethyl acetate were added. After vigorous stirring, the aqueous protion was collected. The organic phase was extracted with 25 mL of diluted sodium bicarbonate. The combined aqueous phases were cooled to 0° C., 20 mL of methylene chloride were added and the mixture was acidified to pH 2 with 5% HCl (about 14 mL). The organic phase was collected and the aqueous mixture was extracted with two 25 mL portions of methylene chloride. The combined organic phases were dried, then concentrated in vacuo to give 1.22 g (93.8% yield) of white solid penicillin-G free acid. The NMR spectrum was consistent with the structure of penicillin-G free acid.

The following two examples illustrate the process of this invention applied to the deallylation of simple aromatic acids.

EXAMPLE 12

To an ice-cooled solution of the allyl ester of benzoic acid (1.00 g, 6.16 mmol) in 15 mL of methylene chloride was added tetrakis(triphenylphosphine)palladium (178 mg, 0.154 mmol). The reaction mixture was stirred until a homogenous solution was obtained. Pyrrolidine (0.540 mL, 6.47 mmol) was added and the resulting mixture was stirred 20 minutes at 0° C., the poured into 20 mL of diluted sodium hydroxide (285 mg NaOH, 7.12 mmol). The organic phase was decanted and the aqueous solution was washed with 5 mL of methylene chloride. After acidification with 5% HCl (about 6 mL) the benzoic acid produce was extracted with methylene chloride using three 10 mL portions. After drying and concentration in vacuo, there were obtained 730 mg (97% yield) of benzoic acid which was isolated as a white solid having a melting point of 122°-123° C.

EXAMPLE 13

To an ice-cooled solution of the allyl ester of trans cinnamic acid (1.0 g, 5.31 mmol) and tetrakis(triphenylphosphine)palladium(0) (150 mg, 0.13 mmol) in 15 mL of methylene chloride was added pyrrolidine (0.466 mL, 5.58 mmol). The resulting mixture was stirred at 0° C. for 50 minutes. It was then poured into 20 mL of diluted sodium hydroxide (5.86 mmol NaOH), the aqueous phase was washed with two 15 mL portions of methylene chloride, then acidified with diluted 5% HCl. The acid was extracted with three 10 mL portions of methylene chloride. The organic phase was then dried over magnesium sulfate and evaporated in vacuo to give 765 mg (97.2% yield) of trans cinnamic acid having a melting point of 133°-134° C. The NMR spectrum was consistent with the structure of trans cinnamic acid.

The following example illustrates the deallylation of the allyl ether of phenol.

EXAMPLE 14

To a solution of allylphenyl ether (1.00 g, 7.45 mmol) in 10 mL of methylene chloride were added tetrakis(triphenylphosphine)palladium(0) (215 mg, 0.186 mmol), triphenylphosphine (215 mg, 0.819 mmol) and pyrrolidine (0.684 mL, 8.198 mmol). The mixture was stirred at room temperature for 4 hours. The reaction mixture was extracted with two 10 mL portions of 5% aqueous sodium hydroxide, and the extracts were acidified with concentrated HCl to a pH of about 1-2. The phenol was extracted with three 10 mL portions of methylene chloride, dried over magnesium sulfate and filtered. After concentration in vacuo, there were obtained 625 mg (89.1% yield) of pure phenol. The NMR spectrum was consistent with the structure of phenol.

What is claimed is:

1. A process for the deprotection of an allyl ester of a carbapenem derivative, said carbapenem derivative being characterized by a 2-substituent of the formula

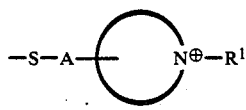

in which A represents a $C_1$–$C_6$ straight or branched chain alkylene group; $R^1$ represents an optionally substituted aliuphatic, cycloaliphatic, cycloaliphatic-aliphatic, aryl, araliphatic, heteroaryl, heteroaraliphatic, heterocyclyl or heterocyclyl-aliphatic radical and

represents a nitrogen-containing aromatic heterocycle attached to the alkylene group A at a ring carbon atom and quanternized by substituent $R^1$ which comprises reacting said allyl ester of the carbapenem derivative with from 1.0 to 1.5 molecular proportions of pyrrolidine and a catalytic amount of an organic-soluble palladium complex having a coordinating phosphine ligand in an inert organic solvent at $-50°$ C. to $30°$ C. during a period of from 10 min. to 4 hrs. to cleave the allyl moiety and recovering the resulting carbapenem derivative.

2. A process as defined in claim 1 wherein said organic soluble palladium complex having a coordinating phosphine ligand is tetrakis(triphenylphosphine)palladium(0).

3. A process as defined in claim 2 wherein from 0.01 to 0.1 mole of tetrakis(triphenylphosphine)palladium(0) are used per mole of said allyl ester.

4. A process as defined in claim 2 wherein said tetrakis(triphenylphosphine)palladium(0) is used in the presence of free triphenylphosphine.

5. A process as defined in claim 4 wherein from 1.5 to 5 moles of triphenylphosphine are used per mole of tetrakis(triphenylphosphine)palladium(0).

* * * * *